(12) United States Patent
Koenemann

(10) Patent No.: US 8,309,728 B2
(45) Date of Patent: *Nov. 13, 2012

(54) NAPHTHALENETETRACARBOXYLIC ACID DERIVATIVES AND THEIR USE AS SEMICONDUCTORS

(75) Inventor: Martin Koenemann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/296,254

(22) Filed: Nov. 15, 2011

(65) Prior Publication Data

US 2012/0059168 A1 Mar. 8, 2012

Related U.S. Application Data

(63) Continuation of application No. 12/097,774, filed as application No. PCT/EP2006/070143 on Dec. 22, 2006, now Pat. No. 8,084,603.

(30) Foreign Application Priority Data

Dec. 23, 2005 (DE) .......................... 10 2005 061 997

(51) Int. Cl.
 C07D 471/00 (2006.01)
 C07D 491/00 (2006.01)
 C07D 498/00 (2006.01)
 C07D 311/78 (2006.01)
(52) U.S. Cl. .......................... 546/66; 549/384
(58) Field of Classification Search ............... 544/66; 546/66; 549/384
 See application file for complete search history.

(56) References Cited

U.S. PATENT DOCUMENTS

| | | | | |
|---|---|---|---|---|
| 7,259,260 B2 * | 8/2007 | Ogiso et al. | ............... | 544/286 |
| 7,605,263 B2 * | 10/2009 | Schmid et al. | ............... | 546/62 |
| 8,084,603 B2 * | 12/2011 | Koenemann | ............... | 544/66 |
| 2003/0153005 A1 * | 8/2003 | Schmid et al. | ............... | 435/7.1 |
| 2005/0176970 A1 | 8/2005 | Marks et al. | | |

FOREIGN PATENT DOCUMENTS

| | | | |
|---|---|---|---|
| DE | 32 35 526 | | 3/1984 |
| DE | 37 03 131 | * | 8/1988 |
| DE | 195 47 209 | | 6/1997 |
| DE | 101 48 172 | * | 4/2003 |
| JP | 2004-93801 | * | 8/2002 |
| JP | 2004-93807 | * | 8/2002 |

OTHER PUBLICATIONS

Tachikawa, et al., Hybrid Density Functional Theory (DFT) Study on Electronic States of Halogen-Substituted Organic-Inorganic Hybrid Compounds: AI-NTCDA, Japanese J. of Applied Physics, vol. 44, No. 6A, 3769-3773 (2005).*

Tachikawa, H. et al., "Hybrid Density Functional Theory (DFT) Study on Electronic States of Halogen-Substituted Organic-Inorganic Hybrid Compounds: AI-NTCDA", Japanese Journal of Applied Physics, vol. 44, No. 6A., pp. 3769-3773, XP002429103 (2005).

Ahrens, M.J. et al., "Self-Assembly of Supramolecular Light-Harvesting Arrays from Covalent Multi-Chromophore Perylene-3,4:9,10-bis (dicarboximide) Building Blocks", J. Am. Chem. Soc., vol. 126, pp. 8284-8294, (2004).

Ahrens, M.J. et al., "Cyanates Perylene-3,4-dicarboximides and Perylene-3, 4:9,10-bis (dicarboximide): Facile Chromophoric Oxidants for Organic Photonics and Electronics", Chem. Mater, vol. 15, pp. 2684-2686 (2003).

Jones, B.A., et al., "High Mobility Air-Stable n-Type Semiconductors with Processing Versatiilty: Dicyanoperylene-3,4:9,10-bis (dicarboximides)", Angew. Chem. vol. 116, pp. 6523-6526 (2004).

Thalacker, C.H., "Supramolecular Assemblies of Naphthalene and Perylene Bisimide Dyes Based on Hydrogen Bonding and Interactions", University ULM, pp. 136 and 147 to 148, (2001).

G. G. Yakobson, et al., "Preparation of decafluoropyrene and its reaction with nitric acid", Inst. Org. Chem., Database CA [Online] Chemical Abstracts Service, Retrieved from STN Database accession No. 1966:482066, 1966, 1 page.

N. V. Martyushina, et al., "Search for nondepolarizing myorelaxants with short duration of action", Inst. Eksp. Med., Database CA [Online] Chemical Abstracts Service, Retreived from STN Database accession No. 1982:544528, 1982, 1 page.

* cited by examiner

*Primary Examiner* — Erich A Leeser

(74) *Attorney, Agent, or Firm* — Oblon, Spivak, McClelland, Maier & Neustadt, L.L.P.

(57) ABSTRACT

The present invention relates to naphthalenetetracarboxylic acid derivates, to a process for their preparation and to their use, especially as an n-type semiconductor.

11 Claims, No Drawings

NAPHTHALENETETRACARBOXYLIC ACID DERIVATIVES AND THEIR USE AS SEMICONDUCTORS

REFERENCE TO PRIOR APPLICATIONS

This application is a Continuation of U.S. application Ser. No. 12/097,774, filed Jun. 17, 2008; which is a 371 of PCT/EP2006/070143, filed Dec. 22, 2006. Priority to German patent application 10 2005 061 997.5, filed Dec. 23, 2005, is claimed.

DESCRIPTION

The present invention relates to naphthalenetetracarboxylic acid derivates, to a process for their preparation and to their use, especially as n-type semiconductors.

In many fields of the electronics industry, organic semiconductors based on low molecular weight or polymeric materials are increasingly also being used in addition to the classical inorganic semiconductors. The former in many cases have advantages over the classical inorganic semiconductors, for example, better substrate compatibility, better processability of the semiconductor components based on them, greater flexibility, reduced costs and the possibility of adjusting their frontier orbital energies to the particular field of use with the methods of molecular design. A main field of use in the electronics industry is that of so-called field-effect transistors (FETs). A great potential for development, for example, in storage elements and integrated optoelectronic devices is ascribed to organic field-effect transistors (OFETs). There is therefore a great need for organic compounds which are suitable as organic semiconductors, in particular n-type semiconductors, and especially for use in organic field-effect transistors.

DE-A-32 35 526 relates to perylene-3,4,9,10-tetracarboximides, which are substituted on the perylene skeleton by alkoxy or alkylthio groups, and also by fluorine, chlorine or bromine, to a process for their preparation and to their use in light-collecting plastics.

DE-A-195 47 209 relates to 1,7-diaryloxy- or 1,7-diarylthio-substituted perylene-3,4,9,10-tetracarboxylic acids and to their dianhydrides and diimides. For their preparation, 1,7-dibromoperylene-3,4,9,10-tetracarboximides are used as intermediates. The preparation of this dibromo compound succeeds starting from perylene-3,4,9,10-tetracarboxylic dianhydride by bromination in the presence of iodine and sulfuric acid.

In J. Am. Chem. Soc. 2004, 126, pp. 8284-8294, M. J. Ahrens et al. describe self-assembling, supermolecular, light-collecting arrays of covalent, multichromophoric perylene-3,4,9,10-bis(dicarboximide) repeat units.

In Chem. Mater. 2003, 15, pp. 2684-2686, M. J. Ahrens, M. J. Fuller and M. R. Wasielewski describe cyano-substituted perylene-3,4-dicarboximides and perylene-3,4,9,10-bis(dicarboximide) and their use as chromophoric oxidizing agents, for example for use in photonics and electronics.

In Angew. Chem. 2004, 116, pp. 6523-6526, B. A. Jones et al. describe the use of dicyanoperylene-3,4,9,10-bis(dicarboximides) as n-semiconductors.

US 2005/0176970 A1 describes n-semiconductors based on substituted perylene-3,4-dicarboximides and perylene-3,4,9,10-bis(dicarboximides). This document quite generally, and without any evidence by way of a preparation example, also describes substituted naphthalene-1,8-dicarboximides and naphthalene-1,4;5,8-bis(dicarboximides) and their use as n-semiconductors. Intermediates mentioned for the preparation of the perylenes are 1,7-dibromoperylene-3,4,9,10-tetracarboxylic dianhydride and the corresponding 1,7-dibromoperylene-3,4,9,10-bis(dicarboximide), and with regard to their preparation, reference is made to the possibility of directly brominating the corresponding starting hydrocarbon compound. Unlike the perylenes, the corresponding 2,6-dibrominated naphthalenes are, however, not obtainable by direct bromination, for example in the presence of iodine and sulfuric acid.

In his thesis, C. H. Thalacker, University of Ulm, 2001, describes supramolecular arrangements of naphthalene- and perylenebisimide dyes based on hydrogen bonds and π-π interactions. On pages 136 and 147 to 148 of this document, the synthesis of 2,6-dibromonaphthalene-1,8;4,5-tetracarboxylic bisanhydride is described, but an imidation of only one of the two anhydride groups did not succeed.

DE 101 48 172 A1 describes naphthalene-1,8;4,5-tetracarboxylic bisimides of the general formula

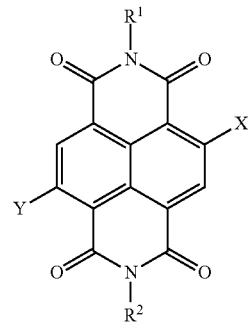

in which

R¹ and R² are each independently hydrogen, substituted or unsubstituted alkyl or substituted or unsubstituted aryl, and X and Y are each independently hydrogen, halogen, amino or a radical of the formula —NHR³ or —OR³, where R³ is —CH₂R⁴, —CHR⁴R⁵ or —CR⁴R⁵R⁶, where R⁴, R⁵, R⁶ are each independently hydrogen, substituted or unsubstituted alkyl, aryl, alkoxy, alkylthio, aryloxy or arylthio, where at least one of the two substituents X and Y is not hydrogen or halogen.

One possible starting material mentioned for the preparation of these compounds is 2,6-dibromonaphthalene-1,8;4,5-tetracarboxylic bisanhydride and, without specific details, reference is made to known methods for preparing the corresponding 2,5-dibromonaphthalene-1,8;4,5-tetracarboximides. In contradiction to this and in agreement with the above-mentioned thesis by Thalacker, working example 4, however, describes the imidation of 2,6-dibromonaphthalene-1,8;4,5-tetracarboxylic dianhydride with 2-ethylhexylamine, which simultaneously substitutes the bromine atoms bonded to the aromatic base structure by 2-ethylhexylamino groups. A workable synthesis for the preparation of 2,6-dibromonaphthalene-1,8;4,5-tetracarboximides is thus disclosed neither in DE 101 48 172 A1 nor in the thesis by Thalacker.

It is an object of the present invention to provide novel compounds which are suitable as n-semiconductors, for example for use in organic field-effect transistors.

This object is achieved by a compound of the general formula I

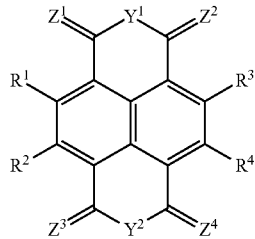

where
at least one of the $R^1$, $R^2$, $R^3$ and $R^4$ radicals is a substituent which is selected from Br, F and CN,
$Y^1$ is O or $NR^a$, where $R^a$ is hydrogen or an organyl radical,
$Y^2$ is O or $NR^b$, where $R^b$ is hydrogen or an organyl radical,
$Z^1$ and $Z^2$ are each independently O or $NR^c$, where $R^c$ is an organyl radical,
$Z^3$ and $Z^4$ are each independently O or $NR^d$, where $R^d$ is an organyl radical,
where, in the case that $Y^1$ is $NR^a$ and at least one of the $Z^1$ and $Z^2$ radicals is $NR^c$, $R^a$ with one $R^c$ radical may also together be a bridging group having 2 to 5 atoms between the flanking bonds, and
where, in the case that $Y^2$ is $NR^b$ and at least one of the $Z^3$ and $Z^4$ radicals is $NR^d$, $R^b$ with one $R^d$ radical may also together be a bridging group having 2 to 5 atoms between the flanking bonds.

In the context of the present invention, the term "alkyl" comprises straight-chain or branched alkyl. It is preferably straight-chain or branched $C_1$-$C_{30}$-alkyl, in particular $C_1$-$C_{20}$-alkyl and most preferably $C_1$-$C_{12}$-alkyl. Examples of alkyl groups are in particular methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, 1,1,3,3-tetramethylbutyl, nonyl, decyl, n-undecyl, n-dodecyl, n-tridecyl, isotridecyl, n-tetradecyl, n-hexadecyl, n-octadecyl and n-eicosyl.

The term alkyl also comprises alkyl radicals, whose carbon chains may be interrupted by one or more nonadjacent groups which are selected from —O—, —S—, —$NR^e$—, —CO— and/or —$SO_2$—, i.e. the termini of the alkyl group are formed by carbon atoms. $R^e$ is preferably hydrogen, alkyl, cycloalkyl, heterocycloalkyl, aryl or hetaryl.

The above remarks on alkyl also apply to the alkyl moieties in alkoxy, alkylamino, alkylthio, alkylsulfinyl and alkylsulfonyl.

In the context of the present invention, the term "alkenyl" comprises straight-chain and branched alkenyl groups which, depending on the chain length, may bear one or more double bonds. Preference is given to $C_2$-$C_{20}$-alkenyl, particular preference to $C_2$-$C_{10}$-alkenyl groups. The term "alkenyl" also comprises substituted alkenyl groups, which may bear, for example, 1, 2, 3, 4 or 5 substituents. Suitable substituents are, for example, cycloalkyl, heterocycloalkyl, aryl, heteroaryl, nitro, cyano, halogen, amino, mono- or di-($C_1$-$C_{20}$-alkyl)amino.

Alkenyl is then, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1-methyl-1,3-butadienyl, 2-methyl-1,3-butadienyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl and the like. The remarks on alkenyl also apply to the alkenyl groups in alkenyloxy, alkenylthio, etc.

The term "alkynyl" comprises unsubstituted or substituted alkynyl groups, which have one or more nonadjacent triple bonds such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like. The remarks on alkynyl also apply to the alkynyl groups in alkynyloxy, alkynylthio, etc.

In the context of the present invention, the term "cycloalkyl" comprises both unsubstituted and substituted cycloalkyl groups, preferably $C_3$-$C_8$-cycloalkyl groups such as cyclopropyl, cyclobutyl, cyclopentyl, cyclohexyl, cycloheptyl or cyclooctyl, in particular $C_5$-$C_8$-cycloalkyl. In the case of substitution, the cycloalkyl groups may bear one or more, for example one, two, three, four or five, $C_1$-$C_8$-alkyl groups.

$C_5$-$C_8$-cycloalkyl which is unsubstituted or may bear one or more $C_1$-$C_6$-alkyl groups is, for example, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl.

The term cycloalkenyl comprises preferably monocyclic, monounsaturated hydrocarbon groups having from 3 to 8, preferably from 5 to 6, carbon ring members, such as cyclopenten-1-yl, cyclopenten-3-yl, cyclohexen-1-yl, cyclohexen-3-yl, cyclohexen-4-yl and the like.

The term bicycloalkyl comprises preferably bicyclic hydrocarbon radicals having from 5 to 10 carbon atoms, such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl, bicyclo[4.4.0]decyl and the like.

In the context of the present invention, the term "aryl" comprises mono- or polycyclic aromatic hydrocarbon radicals which may be unsubstituted or substituted. The term "aryl" preferably represents phenyl, tolyl, xylyl, mesityl, duryl, naphthyl, fluorenyl, anthracenyl, phenanthrenyl or naphthyl, more preferably phenyl or naphthyl, where these aryl groups, in the case of substitution, may generally bear 1, 2, 3, 4 or 5, preferably 1, 2 or 3 substituents which are selected from $C_1$-$C_{18}$-alkyl, $C_1$-$C_6$-alkoxy, cyano, $CONR^fR^g$, $CO_2R^f$, arylazo and heteroarylazo, where arylazo and heteroarylazo are in turn unsubstituted or bear one or more radicals which are each independently selected from $C_1$-$C_{18}$-alkyl, $C_1$-$C_6$-alkoxy and cyano. $R^f$ and $R^g$ are each independently hydrogen, alkyl, cycloalkyl, heterocycloalkyl, aryl or hetaryl.

Aryl, which is unsubstituted or bears one or more radicals which are each independently selected from $C_1$-$C_{18}$-alkyl, $C_1$-$C_6$-alkoxy and cyano is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

In the context of the present invention, the term "heterocycloalkyl" comprises nonaromatic, unsaturated or fully saturated, cycloaliphatic groups having generally from 5 to 8 ring atoms, preferably 5 or 6 ring atoms, in which 1, 2 or 3 of the ring carbon atoms are replaced by heteroatoms selected from oxygen, nitrogen, sulfur and an —$NR^e$— group and which is unsubstituted or substituted by one or more, for example, 1, 2, 3, 4, 5 or 6 $C_1$-$C_6$-alkyl groups. Examples of such heterocycloaliphatic groups include pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl and dioxanyl.

In the context of the present invention, the term "heteroaryl" comprises unsubstituted or substituted, heteroaromatic, mono- or polycyclic groups, preferably the pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl groups, where these heterocycloaromatic groups, in the case of substitution, may generally bear 1, 2 or 3 substituents. The substituents are selected from $C_1$-$C_6$-alkyl, $C_1$-$C_6$-alkoxy, hydroxyl, carboxyl and cyano.

5- to 7-membered heterocycloalkyl or heteroaryl radicals, which are bonded via a nitrogen atom and, if appropriate, comprise further heteroatoms are, for example, pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

Halogen is fluorine, chlorine, bromine or iodine.

Specific examples of the radicals mentioned in the following formulae and their substituents are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9- triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di(o-tolyl)phosphino and diphenylphosphinoxido;

fluorine, chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl)-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6- tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Preferred fluorinated radicals are the following:

2,2,2-trifluoroethyl, 2,2,3,3,4,4,4-heptafluorobutyl, 2,2,3,3,3-pentafluoropropyl, 1H,1H-pentadecafluorooctyl, 2,2-difluoroethyl, 2,2,2-trifluoro-1-phenylethylamine, 1-benzyl-2,2,2-trifluoroethyl, 1H,1H-perfluoroheptyl, 1H,1H-perfluorononyl, 2-bromo-2,2-difluoroethyl, 2,2,2-trifluoro-1,1-dimethylethyl, 2,2,2-trifluoro-1-(methyl)ethyl, 1,1,1-trifluoroisopropyl, 2,2,2-trifluoro-1-pyridin-2-ylethyl, 2,2,3,3,4,4,5,5,6,6,7,7,8,8,9,9,10,10-nonadecafluorodecyl, 3,5,7,8-tetrabromo-2,2,3,4,4,5,6,6,7,8,8-undecafluorooctyl, 2,2,3,3,4,4,5,5-octafluoropentyl, 1H,1H-perfluoropentyl, 2,2-difluoropropyl, 2,2,2-trifluoro-1-(4-methoxyphenyl)ethylamine, 2,2,2-trifluoro-1-phenylethylamine, 2,2-difluoro-1-phenylethylamine, 1-(4-bromophenyl)-2,2,2-trifluoroethyl, 3-bromo-3,3-difluoropropyl, 3,3,3-trifluoropropylamine, 3,3,3-trifluoro-n-propyl, 1H,1H,2H,2H-perfluorodecyl, 3-(perfluorooctyl)propyl, 4,4-difluorobutyl, 4,4,4-trifluorobutyl, 5,5,6,6,6-pentafluorohexyl, 2-fluorophenyl, pentafluorophenyl, 2,3,5,6-tetrafluorophenyl, 4-cyano-(2,3,5,6)-tetrafluorophenyl, 4-carboxy-2,3,5,6-tetrafluorophenyl, 2,4-difluorophenyl, 2,4,5-trifluorophenyl, 2,4,6-trifluorophenyl, 2,5-difluorophenyl, 2-fluoro-5-nitrophenyl, 2-fluoro-5-trifluoromethylphenyl, 2-fluoro-5-methylphenyl, 2,6-difluorophenyl, 4-carboxamido-2,3,5,6-tetrafluorophenyl, 2-bromo-4,6-difluorophenyl, 4-bromo-2-fluorophenyl, 2,3-difluorophenyl, 4-chloro-2-fluorophenyl, 2,3,4-trifluorophenyl, 2-fluoro-4-iodophenyl, 4-bromo-2,3,5,6-tetrafluorophenyl, 2,3,6-trifluorophenyl, 2-bromo-3,4,6-trifluorophenyl, 2-bromo-4,5,6-trifluorophenyl, 4-bromo-2,6-difluorophenyl, 2,3,4,5-tetrafluorophenyl, 2,4-difluoro-6-nitrophenyl, 2-fluoro-4-nitrophenyl, 2-chloro-6-fluorophenyl, 2-fluoro-4-methylphenyl, 3-chloro-2,4-difluorophenyl, 2,4-dibromo-6-fluorophenyl, 3,5-dichloro-2,4-difluorophenyl, 4-cyano-1-fluorophenyl, 1-chloro-4-fluorophenyl, 2-fluoro-3-trifluoromethylphenyl, 2-trifluoromethyl-6-fluorophenyl, 2,3,4,6-tetrafluorophenyl, 3-chloro-2-fluorophenyl, 5-chloro-2-fluorophenyl, 2-bromo-4-chloro-6-fluorophenyl, 2,3-dicyano-4,5,6-trifluorophenyl, 2,4,5-trifluoro-3-carboxyphenyl, 2,3,4-trifluoro-6-carboxyphenyl, 2,3,5-trifluorophenyl, 4-trifluoromethyl-2,3,5,6-tetrafluorophenyl, 1-fluoro-5-carboxyphenyl, 2-chloro-4,6-difluorophenyl, 6-bromo-3-chloro-2,4-difluorophenyl, 2,3,4-trifluoro-6-nitrophenyl, 2,5-difluoro-4-cyanophenyl, 2,5-difluoro-4-trifluoromethylphenyl, 2,3-difluoro-6-nitrophenyl, 4-trifluoromethyl-2,3-difluorophenyl, 2-bromo-4,6-difluorophenyl, 4-bromo-2-fluorophenyl, 2-nitrotetrafluorophenyl, 2,2',3,3',4',5,5',6,6'-nonabiphenyl, 2-nitro-3,5,6-trifluorophenyl, 2-bromo-6-fluorophenyl, 4-chloro-2-fluoro-6-iodophenyl, 2-fluoro-6-carboxyphenyl, 2,4-difluoro-3-trifluorophenyl, 2-fluoro-4-trifluorophenyl, 2-fluoro-4-carboxyphenyl, 4-bromo-2,5-difluorophenyl, 2,5-dibromo-3,4,6-trifluorophenyl, 2-fluoro-5-methylsulfonylphenyl, 5-bromo-2-fluorophenyl, 2-fluoro-4-hydroxymethylphenyl, 3-fluoro-4-bromomethylphenyl, 2-nitro-4-trifluoromethylphenyl, 4-trifluoromethylphenyl, 2-bromo-4-trifluoromethylphenyl, 2-bromo-6-chloro-4-(trifluoromethyl)phenyl, 2-chloro-4-trifluoromethylphenyl, 3-nitro-4-(trifluoromethyl)phenyl, 2,6-dichloro-4-(trifluoromethyl)phenyl, 4-trifluorophenyl, 2,6-dibromo-4-(trifluoromethyl)phenyl, 4-trifluoromethyl-2,3,5,6-tetrafluorophenyl, 3-fluoro-4-trifluoromethylphenyl, 2,5-difluoro-4-trifluoromethylphenyl, 3,5-difluoro-4-trifluoromethylphenyl, 2,3-difluoro-4-trifluoromethylphenyl, 2,4-bis(trifluoromethyl)phenyl, 3-chloro-4-trifluoromethylphenyl, 2-bromo-4,5-di(trifluoromethyl)phenyl, 5-chloro-2-nitro-4-(trifluoromethyl)phenyl, 2,4,6-tris(trifluoromethyl)phenyl, 3,4-bis(trifluoromethyl)phenyl, 2-fluoro-3-trifluoromethylphenyl, 2-iodo-4-trifluoromethylphenyl, 2-nitro-4,5-bis(trifluoromethyl)phenyl, 2-methyl-4-(trifluoromethyl)phenyl, 3,5-dichloro-4-(trifluoromethyl)phenyl, 2,3,6-trichloro-4-(trifluoromethyl)phenyl, 4-(trifluoromethyl)benzyl, 2-fluoro-4-(trifluoromethyl)benzyl, 3-fluoro-4-(trifluoromethyl)benzyl, 3-chloro-4-(trifluoromethyl)benzyl, 4-fluorophenethyl, 3-(trifluoromethyl)phenethyl, 2-chloro-6-fluorophenethyl, 2,6-dichlorophenethyl, 3-fluorophenethyl, 2-fluorophenethyl, (2-trifluoromethyl)phenethyl, 4-trifluoromethylphenethyl, 2,3-difluorophenethyl, 3,4-difluorophenethyl, 2,4-difluorophenethyl, 2,5-difluorophenethyl, 3,5-difluorophenethyl, 2,6-difluorophenethyl, 4-(4-fluorophenyl)phenethyl, 3,5-di(trifluoromethyl)phenethyl, pentafluorophenethyl, 2,4-di(trifluoromethyl)phenethyl, 2-nitro-4-(trifluoromethyl)phenethyl, (2-fluoro-3-trifluoromethyl)phenethyl, (2-fluoro-5-trifluoromethyl)phenethyl, (3-fluoro-5-trifluoromethyl)phenethyl, (4-fluoro-2-trifluoromethyl)phenethyl, (4-fluoro-3-trifluoromethyl)phenethyl, (2-fluoro-6-trifluoromethyl)phenethyl, (2,3,6-trifluoro)phenethyl, (2,4,5-trifluoro)phenethyl, (2,4,6-trifluoro)phenethyl, (2,3,4-trifluoro)phenethyl, (3,4,5-trifluoro)phenethyl, (2,3,5-trifluoro)phenethyl, (2-chloro-5-fluoro)phenethyl, (3-fluoro-4-trifluoromethyl)phenethyl, (2-chloro-5-trifluoromethyl)phenethyl, (2-fluoro-3-chloro-5-trifluoromethyl)phenethyl, (2-fluoro-3-chloro)phenethyl, (4-fluoro-3-chloro)phenethyl, (2-fluoro-4-chloro)phenethyl, (2,3-difluoro-4-methyl)phenethyl, 2,6-difluoro-3-chlorophenethyl, (2,6-difluoro-3-methyl)phenethyl, (2-trifluoromethyl-5-chloro)phenethyl, (6-chloro-2-fluoro-5-methyl)phenethyl, (2,4-dichloro-5-fluoro)phenethyl, 5-chloro-2-fluorophenethyl, (2,5-difluoro-6-chloro)phenethyl, (2,3,4,5-tetrafluoro)phenethyl, (2-fluoro-4-trifluoromethyl)phenethyl, 2,3-(difluoro-4-trifluoromethyl)phenethyl, (2,5-di(trifluoromethyl))phenethyl, 2-fluoro-3,5-dibromophenethyl, (3-fluor-4-nitro)phenethyl, (2-bromo-4-trifluoromethyl)phenethyl, 2-(bromo-5-fluoro)phenethyl, (2,6-difluoro-4-bromo)phenethyl, (2,6-difluoro-4-chloro)phenethyl, (3-chloro-5-fluoro)phenethyl, (2-bromo-5-trifluoromethyl)phenethyl and the like.

In a specific embodiment, the compounds of the formula I are not those in which $Z^1$, $Z^2$, $Z^3$, $Z^4$, $Y^1$ and $Y^2$ are O and the $R^1$ to $R^4$ radicals are selected from hydrogen and bromine.

More specifically, the compounds of the formula I are not those in which $Z^1$, $Z^2$, $Z^3$, $Z^4$, $Y^1$ and $Y^2$ are O and $R^1$ and $R^4$ or $R^2$ and $R^3$ are both bromine. In other words, in a specific embodiment, 2,6-dibromonaphthalene-1,8;4,5-tetracarboxylic dianhydrides are excluded from the compounds of the formula I.

Preference is given to compounds of the formula I, where $R^1$, $R^2$, $R^3$ and $R^4$ are each bromine or are each fluorine or are each cyano.

Preference is further given to compounds of the formula I, where three of the $R^1$, $R^2$, $R^3$ and $R^4$ radicals are each bromine or are each fluorine or are each cyano, and the remaining radical is hydrogen.

Preference is further given to compounds of the formula I, where $R^1$ and $R^2$ are each independently selected from fluorine and cyano, and $R^3$ and $R^4$ are each hydrogen. In a preferred embodiment, $R^1$ and $R^2$ are then each fluorine or are each cyano.

Preference is further given to compounds where $R^1$ and $R^3$ are each independently selected from fluorine and cyano, and $R^2$ and $R^4$ are each hydrogen. In a preferred embodiment, $R^1$ and $R^3$ are then each fluorine or are each cyano.

Preference is further given to compounds where $R^1$ and $R^4$ are each independently selected from fluorine and cyano, and $R^2$ and $R^3$ are each hydrogen. In a preferred embodiment, $R^1$ and $R^4$ are then each fluorine or are each cyano.

Preference is further given to compounds where $R^1$ and $R^2$ are each bromine and $R^3$ and $R^4$ are each hydrogen.

Preference is further given to compounds where one of the $R^1$, $R^2$, $R^3$ and $R^4$ radicals is bromine or is fluorine or is cyano, and the remaining radicals are each hydrogen.

Particular preference is given to compounds of the formula I.a

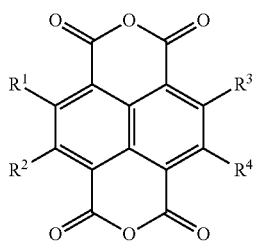

(I.a)

in which
$R^1$, $R^2$, $R^3$ and $R^4$ are each as defined above.

With regard to the definitions of the substituents $R^a$ and $R^b$ in the compounds of the formula I, reference is made to the remarks made at the outset.

$R^a$ and $R^b$ are preferably each independently hydrogen or unsubstituted or substituted alkyl, alkenyl, alkadienyl, alkynyl, cycloalkyl, bicycloalkyl, cycloalkenyl, heterocycloalkyl, aryl or heteroaryl.

More preferably, at least one of the $R^a$ and $R^b$ radicals is a radical with electron-withdrawn substituents.

In a specific embodiment, at least one of the $R^a$ and $R^b$ radicals is a radical mono- or polysubstituted by fluorine. More preferably, both $R^a$ and $R^b$ are a radical mono- or polysubstituted by fluorine. With regard to suitable fluorinated radicals, reference is likewise made to the remarks made at the outset.

In a further specific embodiment, the $R^a$ and $R^b$ radicals are identical.

Particular preference is further given to compounds of the general formula I.b

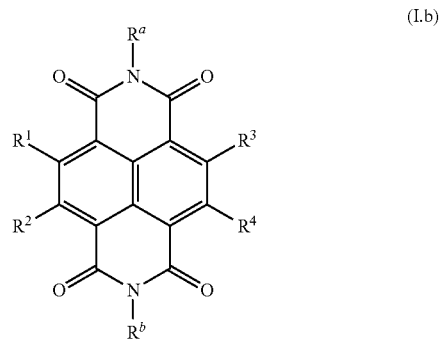

(I.b)

in which
$R^1$, $R^2$, $R^3$ and $R^4$ are each as defined above and
$R^a$ and $R^b$ each independently have one of the definitions specified above.

With regard to suitable and preferred $R^1$, $R^2$, $R^3$, $R^4$, $R^a$ and $R^b$ radicals, reference is made to the above remarks in their entirety.

A further preferred embodiment is that of compounds of the general formula I.c

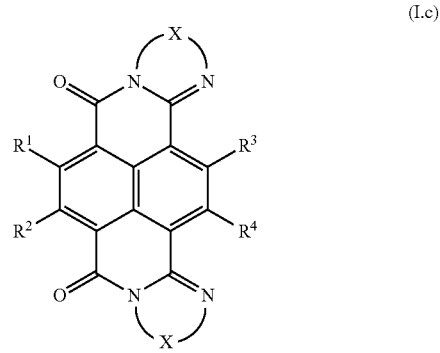

(I.c)

where
$R^1$, $R^2$, $R^3$ and $R^4$ are each as defined above and
X is a divalent bridging group having from 2 to 5 atoms between the flanking bonds,
and the structural isomers thereof.

The bridging groups X, together with the N—C=N group to which they are bonded, are preferably a 5- to 8-membered heterocycle which, if appropriate, is fused singly, doubly or triply to cycloalkyl, heterocycloalkyl, aryl and/or hetaryl, where the fused groups may each independently bear one, two, three or four substituents selected from alkyl, alkoxy, cycloalkyl, aryl, halogen, hydroxy, thiol, polyalkylene oxide, polyalkylenimine, COOH, carboxylate, $SO_3H$, sulfonate, $NE^1E^2$, alkylene-$NE^1E^2$, nitro and cyano, where $E^1$ and $E^2$ are each independently hydrogen, alkyl, cycloalkyl, heterocycloalkyl, aryl or hetaryl, and/or X may have one, two or three substituents which are selected from optionally substituted alkyl, optionally substituted cycloalkyl and optionally substituted aryl, and/or X may be interrupted by 1, 2 or 3 optionally substituted heteroatoms.

The bridging groups X are preferably selected from groups of the formulae

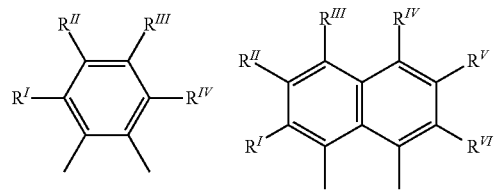

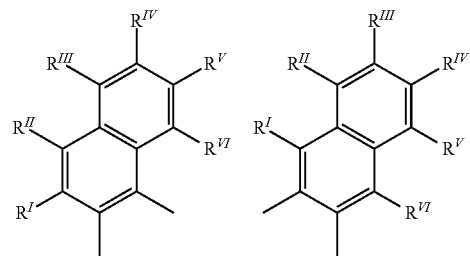

in which

R$^I$, R$^{II}$, R$^{III}$, R$^{IV}$, R$^V$ and R$^{VI}$ are each independently hydrogen, alkyl, alkoxy, cycloalkyl, cycloalkoxy, heterocycloalkyl, heterocycloalkoxy, aryl, aryloxy, hetaryl, hetaryloxy, halogen, hydroxyl, thiol, polyalkylene oxide, polyalkyleneimine, COOH, carboxylate, SO$_3$H, sulfonate, NE$^1$E$^2$, alkylene-NE$^1$E$^2$, nitro, alkoxycarbonyl, acyl or cyano, where E$^1$ and E$^2$ are each independently hydrogen, alkyl, cycloalkyl, heterocycloalkyl, aryl or hetaryl.

Some particularly preferred inventive compounds are reproduced below:

(1)
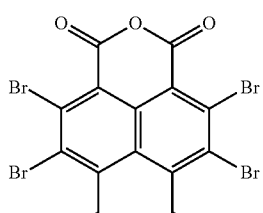

(2)
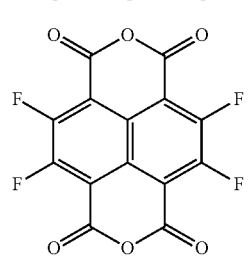

(3)
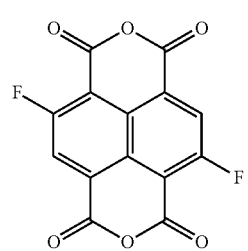

-continued (4)
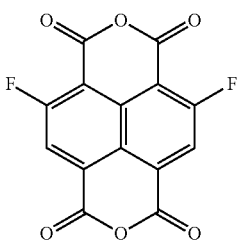

(5)
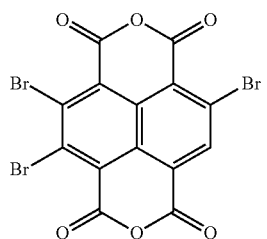

(6)
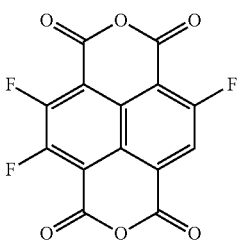

(7)
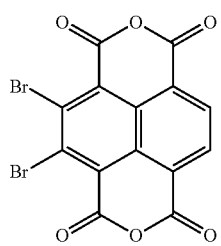

(8)
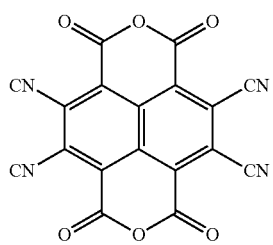

(9)
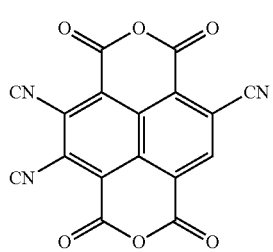

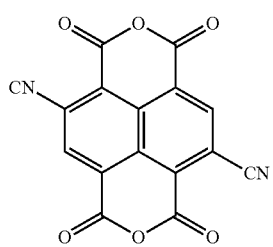
(10)
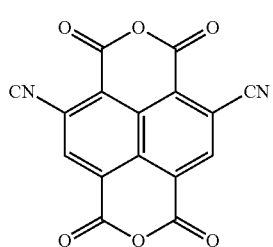
(11)
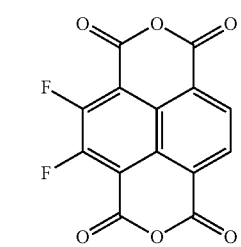
(12)
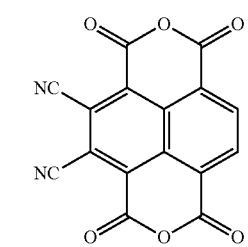
(13)
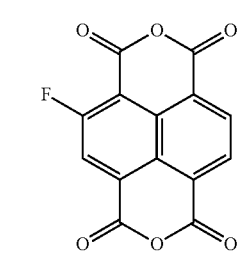
(14)
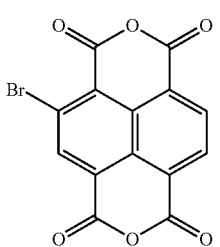
(15)
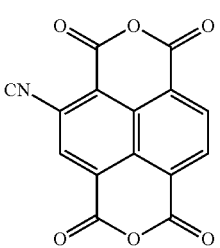
(16)
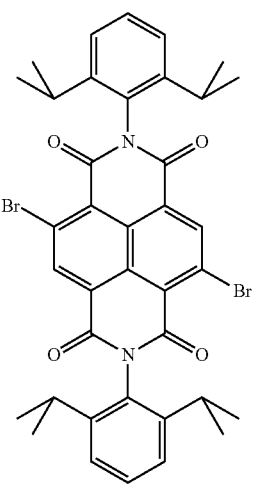
(17)
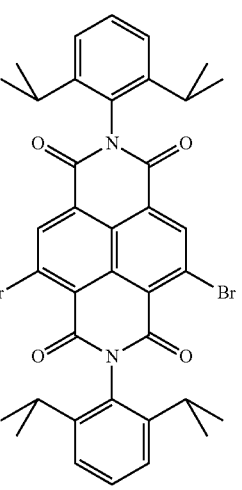
(18)

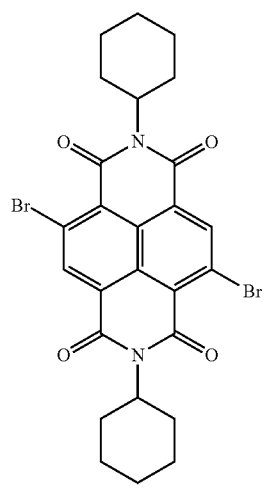
(19)
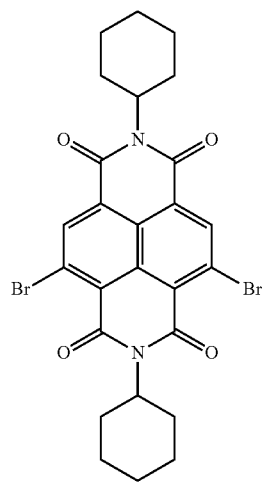
(20)
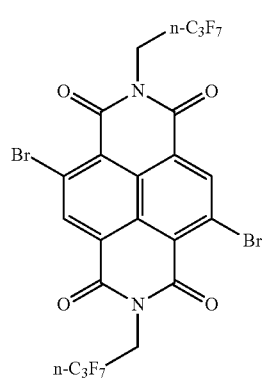
(21)
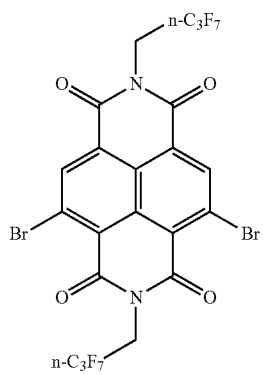
(22)
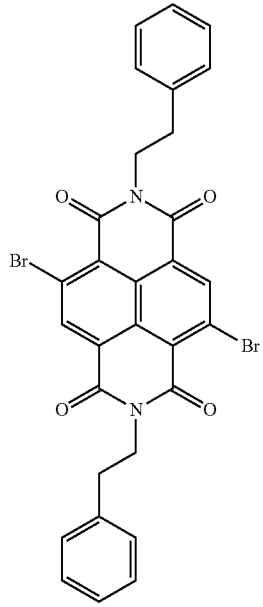
(23)
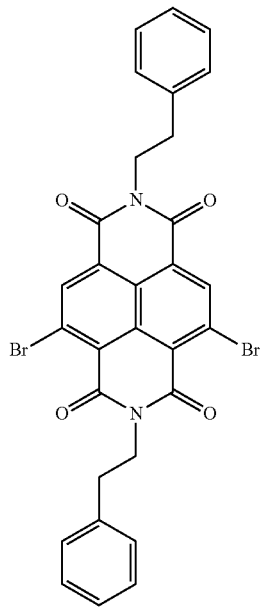
(24)

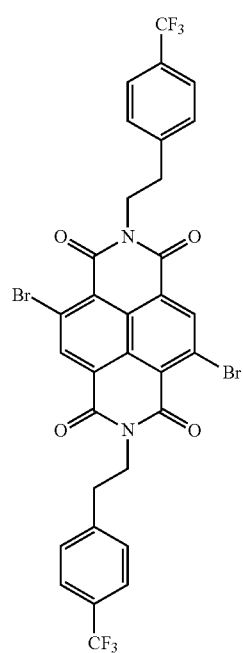
(25)
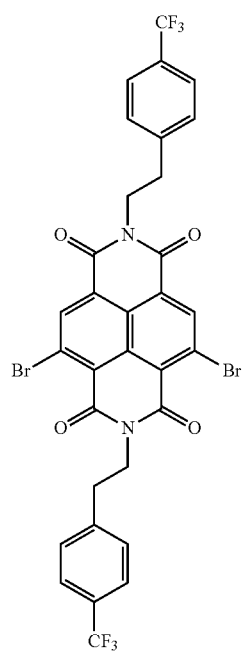
(26)
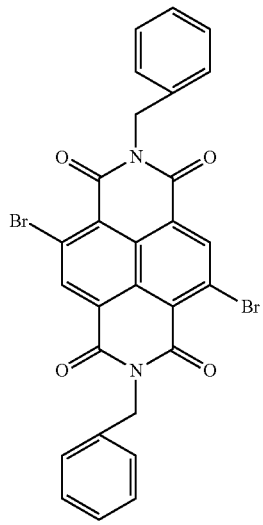
(27)
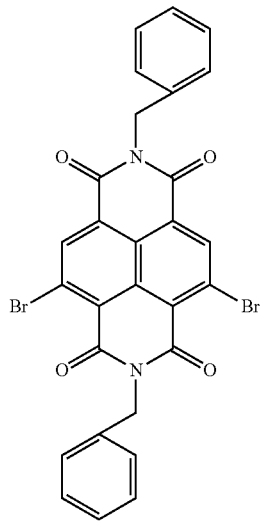
(28)
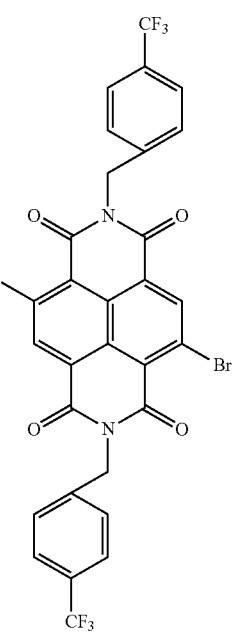
(29)

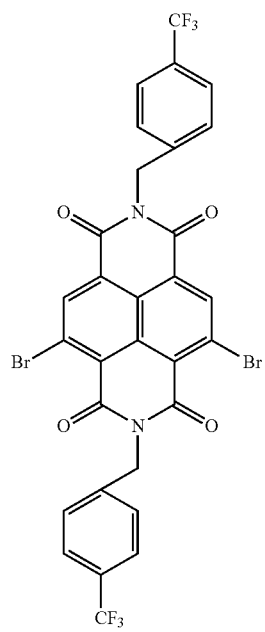
(30)
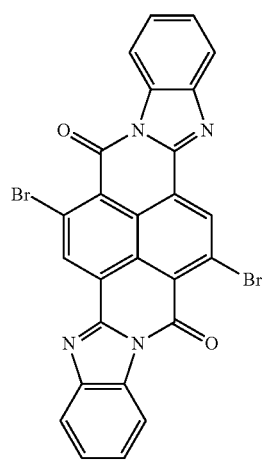
(31)
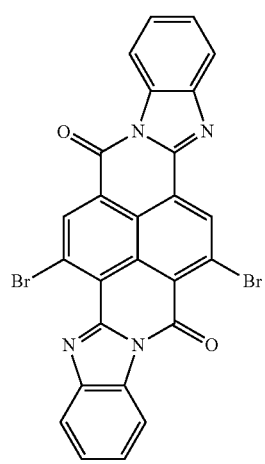
(32)
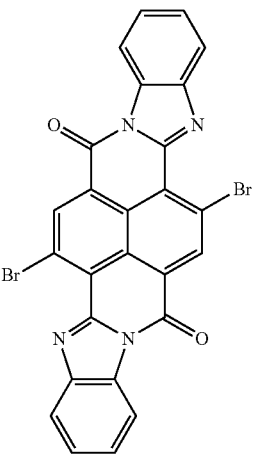
(33)
(34)
(35)

(36)
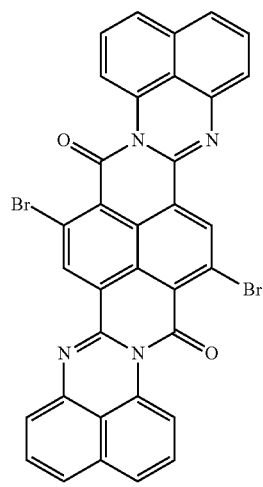
(37)
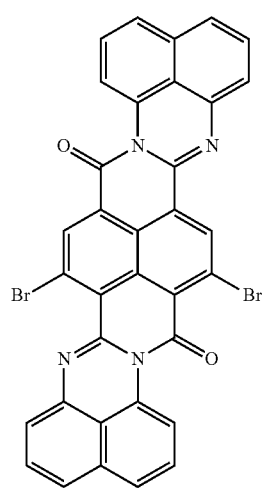
(38)
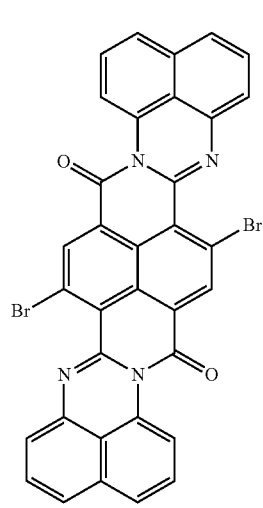
(39)
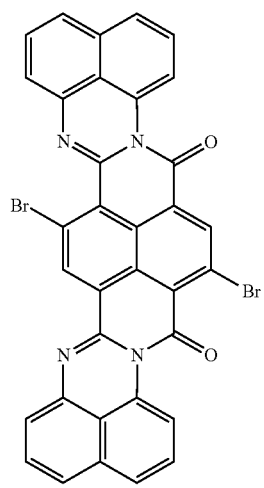
(40)
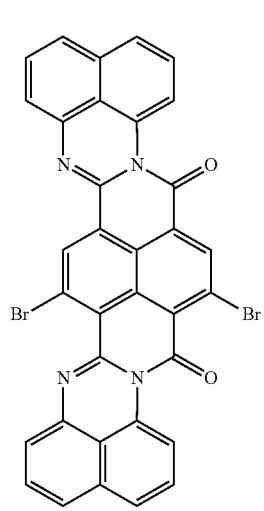
(41)
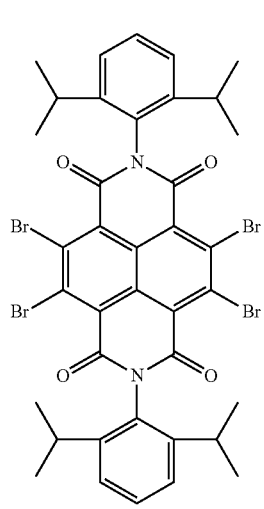

(42)

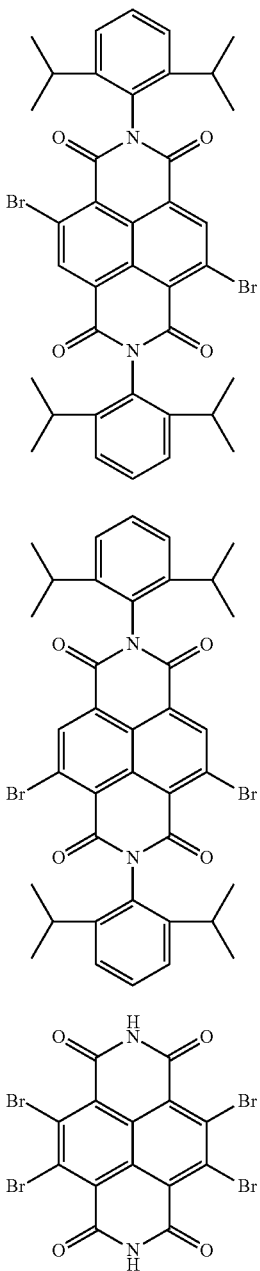

(43)

(44)

It has now been found that, surprisingly, the use of oleum which has a concentration of more than 20%, and in particular of at least 28%, (for example, use of 30% oleum) as a solvent in the bromination of naphthalenetetracarboxylic bisanhydride surprisingly affords the tetrabromo bisanhydride. It has also been found that this tetrabromo bisanhydride can be subjected to

- a full substitution of the bromine atoms by fluorine atoms or cyano groups,
- a partial substitution of the bromine atoms by hydrogen, or
- a partial substitution of the bromine atoms by fluorine atoms or cyano groups with simultaneous partial substitution by hydrogen.

The invention therefore further provides a process for preparing compounds of the formula I.a

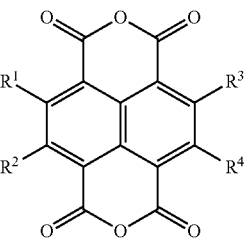

(I.a)

in which
at least one of the $R^1$, $R^2$, $R^3$ and $R^4$ radicals is a substituent which is selected from Br, F and CN, and the remaining radicals are each hydrogen,
by
i) subjecting naphthalene-1,8;4,5-tetracarboxylic dianhydride to a bromination with dibromoisocyanuric acid in the presence of more than 20% oleum to obtain 2,3,6,7-tetrabromonaphthalene-1,8;4,5-tetracarboxylic dianhydride

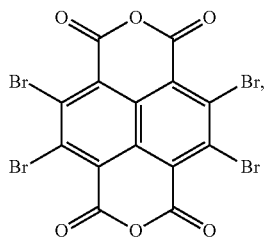

ii) if appropriate subjecting the 2,3,6,7-tetrabromonaphthalene-1,8;4,5-tetracarboxylic dianhydride to a substitution of the bromine atoms by fluorine or by cyano groups, or subjecting the 2,3,6,7-tetrabromonaphthalene-1,8;4,5-tetracarboxylic dianhydride to a partial substitution of the bromine atoms by hydrogen and, if appropriate, by fluorine or by cyano groups,
iii) if appropriate, subjecting the compounds obtained in step ii) to at least one separation and/or purification step.

Step i)
For the reaction in step i), preference is given to using at least 25%, in particular at least 28% oleum (for example, 30% oleum).

The molar ratio of dibromoisocyanuric acid to naphthalene-1,8;4,5-tetracarboxylic bisanhydride is preferably in a range of from about 4:1 to 0.9:1, more preferably from 3:1 to 0.9:1. The molar ratio is in particular from 4:1 to 1.5:1, especially from 2.5:1 to 1.5:1.

Step ii)
Suitable process conditions for the aromatic nucleophilic substitution of bromine atoms or chlorine atoms by fluorine atoms (halo-dehalogenation) are known in principle. Suitable conditions for halo-dehalogenation are described, for example, in J. March, Advanced Organic Chemistry, 4th edition, John Wiley & Sons publishers (1992), p. 659 and also in DE-A-32 35 526. Reference is made here to this disclosure.

In a first embodiment, the reaction in step ii) is an exchange of the bromine atoms for fluorine atoms, if appropriate with a partial dehalogenation. To introduce the fluorine groups, preference is given to using an alkali metal fluoride, in particular KF, NaF or CsF.

Preferred solvents for the halogen exchange in step ii) are aprotic polar solvents such as dimethylformamide, N-methylpyrrolidone, $(CH_3)_2SO$, dimethyl sulfone or in particular sulfolane. Preference is given to subjecting the solvents before use to drying to remove water by customary methods known to those skilled in the art. This applies especially to the removal of residual amounts of water from sulfolane.

For the halogenic exchange in step ii), it is additionally possible to use a complexing agent, for example, a crown ether. These include, for example, [12]crown-4, [15]crown-5, [18]crown-6, [21]crown-7, [24]crown-8, etc. The complexing agent is selected according to its capability of complexing the alkali metals of the alkali metal halides used for the halogen exchange. When KF is used to introduce the fluorine groups, the complexing agent used is preferably [18]crown-6.

Further suitable phase transfer catalysts for use in step ii) are, for example, selected from 2-azaallenium compounds, carbophosphazenium compounds, aminophosphonium compounds and diphosphazenium compounds. A. Pleschke, A. Marhold, M. Schneider, A. Kolomeitsev and G. V. Röschenthaler give, in Journal of Fluorine Chemistry 125, 2004, 1031-1038, a review of further suitable phase transfer catalysts. Reference is made to the disclosure of this document. In a preferred embodiment, 2-azaallenium compounds such as (N,N-dimethylimidazolidino)-tetramethylguanidinium chloride ($CNC^+$) are used. Particular preference is then given to using sulfolane as the solvent. The use amount of the aforementioned phase transfer catalysts is preferably from 0.1 to 20% by weight, more preferably from 1 to 10% by weight, based on the weight of the rylene compound used.

In the case of the reaction with alkali metal fluorides in an anhydrous, aprotic polar solvent, not only a halogen exchange but generally also a dehalogenation is effected to a certain degree. The resulting mixtures of dihalo-, trihalo- and/or tetrahalonaphthalenetetracarboxylic anhydrides may subsequently be subjected to a separation.

In a further embodiment, the reaction in step ii) is an exchange of the bromine atoms for cyano groups, if appropriate with a partial dehalogenation. Suitable process conditions for the cyano-dehalogenation are likewise described in J. March, Advanced Organic Chemistry, 4th edition, John Wiley & Sons publishers (1992), pp. 660-661 and also in WO 2004/029028. These include, for example, the reaction with copper cyanide. Also suitable are alkali metal cyanides, such as KCN and NaCN, and also zinc cyanide in polar aprotic solvents in the presence of Pd(II) salts or copper or nickel complexes. Preferred polar aprotic solvents are those mentioned above for the halogen exchange.

The separation and/or purification in step iii) may be effected by customary methods known to those skilled in the art, such as extraction, distillation, recrystallization, separation on suitable stationary phases, and a combination of these measures.

It has been found that, surprisingly, halogen- or cyano-substituted naphthalene-1,8;4,5-tetracarboximides unobtainable to date can be obtained when naphthalene-1,8;4,5-tetracarboxylic dianhydride is subjected first to a bromination, then to substitution of a bromine by fluorine or cyano groups (if appropriate, combined with a partial dehalogenation) and subsequently an imidation. It has also been found that halogen- or cyano-substituted naphthalene-1,8;4,5-tetracarboximides unobtainable to date can be obtained when naphthalene-1,8;4,5-tetracarboxylic dianhydride is subjected first to an imidation, then to a bromination and subsequently, if appropriate, to a substitution of the bromine by fluorine or cyano groups (if appropriate, combined with a partial dehalogenation). In both process variants, an imidation of the bromine-substituted naphthalene-1,8;4,5-tetracarboxylic dianhydride is avoided.

The invention therefore further provides a process for preparing compounds of the formula

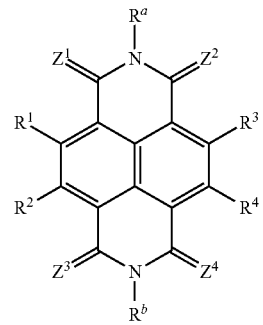

in which
at least one of the $R^1$, $R^2$, $R^3$ and $R^4$ radicals is a substituent which is selected from Br, F and CN, and the remaining radicals are each hydrogen,
$Z^1$, $Z^2$, $Z^3$ and $Z^4$ are each O,
$R^a$ and $R^b$ are each independently hydrogen or unsubstituted or substituted alkyl, alkenyl, alkadienyl, alkynyl, cycloalkyl, bicycloalkyl, cycloalkenyl, heterocycloalkyl, aryl or heteroaryl,
or
one of the $Z^1$ or $Z^2$ radicals is $NR^c$, and $R^a$ and $R^c$ together are a bridging group having 2 to 5 atoms between the flanking bonds, and/or one of the $Z^3$ or $Z^4$ radicals is $NR^d$, and $R^b$ and $R^d$ together are a bridging group having from 2 to 5 atoms between the flanking bonds, by
a1) subjecting naphthalene-1,8;4,5-tetracarboxylic dianhydride to a bromination with N,N'-dibromoisocyanuric acid to obtain a compound of the general formula I.a

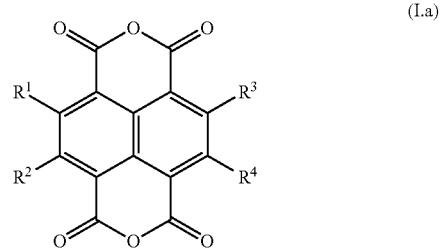

(I.a)

in which two or three or four of the $R^1$, $R^2$, $R^3$ and $R^4$ radicals are each Br, and the remaining radicals are each hydrogen,
b1) subjecting the compound of the formula I.a obtained in step a1) to a substitution of the bromine by fluorine or cyano groups, and also, if appropriate, partly by hydrogen,
c1) subjecting the compound obtained in step b1) to a reaction with an amine of the formula $R^a$—$NH_2$ and, if appropriate, an amine of the formula $R^b$—$NH_2$,
Or
subjecting the compound obtained in step b1) to a reaction with an amine of the formula $H_2N$—X—$NH_2$, where X is a divalent bridging group having from 2 to 5 atoms between the flanking bonds.

The invention further provides a process for preparing compounds of the formula

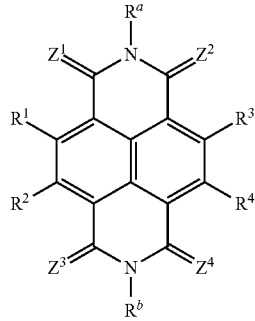

(I.a21)

in which
at least one of the R¹, R², R³ and R⁴ radicals is a substituent which is selected from Br, F and CN, and the remaining radicals are each hydrogen,
$Z^1$, $Z^2$, $Z^3$ and $Z^4$ are each O,
$R^a$ and $R^b$ are each independently hydrogen or unsubstituted or substituted alkyl, alkenyl, alkadienyl, alkynyl, cycloalkyl, bicycloalkyl, cycloalkenyl, heterocycloalkyl, aryl or heteroaryl,
or
one of the $Z^1$ or $Z^2$ radicals is $NR^c$, and $R^a$ and $R^c$ together are a bridging group having 2 to 5 atoms between the flanking bonds, and/or one of the $Z^3$ or $Z^4$ radicals is $NR^d$, and $R^b$ and $R^d$ together are a bridging group having from 2 to 5 atoms between the flanking bonds, by a2) subjecting naphthalene-1,8;4,5-tetracarboxylic dianhydride to a reaction with an amine of the formula $R^a$—$NH_2$ and, if appropriate, an amine of the formula $R^b$—$NH_2$ to obtain at least one compound of the general formula I.a21)

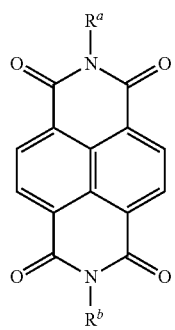

(I.a21)

where $R^b$ may also be as defined for $R^a$,
or
subjecting naphthalene-1,8;4,5-tetracarboxylic dianhydride to a reaction with an amine of the formula $H_2N$—X—$NH_2$ to obtain at least one compound of the general formula I.a22)

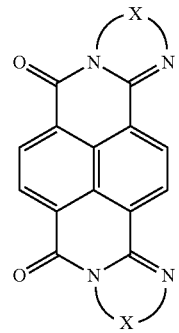

(I.a22)

or an isomer thereof, where X is a divalent bridging group having from 2 to 5 atoms between the flanking bonds,
b2) subjecting the compound(s) obtained in step a2) to a bromination with N,N'-dibromoisocyanuric acid,
c2) if appropriate, subjecting the compound(s) obtained in step b2) to a substitution of the bromine by fluorine or cyano groups, and also, if appropriate, partly by hydrogen.

Step a1) and Step b2)

In a first embodiment, the bromination in steps a1) and b2) is effected using oleum which has a concentration of more than 20% (for example by use of 30% oleum) as a solvent in the bromination to obtain a tetrabrominated compound as described above. For the reaction, preference is then given to using at least 25%, in particular at least 28% oleum (for example 30% oleum).

In a second embodiment, the bromination is effected in steps a1) and b2) using oleum which has a concentration of at most 20%. In that case, predominantly dibrominated compounds are obtained. The ratio of dibromoisocyanuric acid to naphthalene-1,8;4,5-tetracarboxylic dianhydride is then preferably within a range from 1.5:1 to 1:1, especially from 1.25:1 to 1:1.

In a preferred embodiment of the second process variant, the naphthalene-1,8;4,5-tetracarboxylic dianhydride is reacted in step a2) by using amines of the formula $R^a$—$NH_2$ and, if appropriate, one of the formula $R^b$—$NH_2$ or amines of the formula $H_2N$—X—$NH_2$, where $R^a$, $R^b$ and X are each groups which cannot be brominated by reaction with dibromocyanuric acid in step b2). The $R^a$ and $R^b$ radicals are then preferably alkyl, cycloalkyl, bicycloalkyl, heterocycloalkyl, aryl or heteroaryl, which may be substituted by radicals which cannot be exchanged for bromine. Since an at least partial bromination of the $R^a$, $R^b$ and X groups is, however, generally uncritical and may possibly even be advantageous in the case of use of compounds of the formula I as semiconductors, it is also possible to use brominatable groups, in which case the amount of dibromocyanuric acid used for the bromination in step b2) has to be increased if appropriate.

Step b1) and Step c2)

Suitable process conditions for the aromatic nucleophilic substitution of bromine atoms by other halogen atoms (halodehalogenation), for example fluorine, or by cyano groups, are those described above in step ii), to which reference is made here.

Step c1) and Step a2)

When the imidation in step c1) is effected by subjecting the compound obtained in step b1) to a reaction with an amine of the formula $R^a$—$NH_2$ and, if appropriate, an amine of the formula R$^b$—NH$_2$, the result is at least one compound of the general formula I.c1)

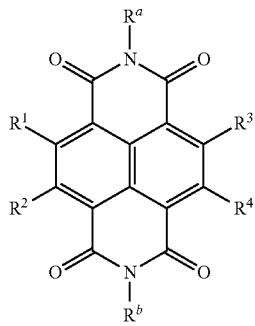

(I.c1)

in which the R$^2$, R$^3$ and R$^4$ radicals, which are each Br in the compound Ia) obtained in step a), are each F or CN, and some of the R$^1$, R$^2$, R$^3$ and R$^4$ radicals, which are each Br in the compound Ia) obtained in step a), may also be hydrogen, where R$^b$ may also be as defined for R$^a$ (if only one amine of the formula R$^a$—NH$_2$ is used for the imidation).

When the imidation in step c1) is effected by subjecting the compound obtained in step b1) to a reaction with an amine of the formula H$_2$N—X—NH$_2$ where X is a divalent bridging group having from 2 to 5 atoms between the flanking bonds, the result is at least one compound of the general formula I.c2)

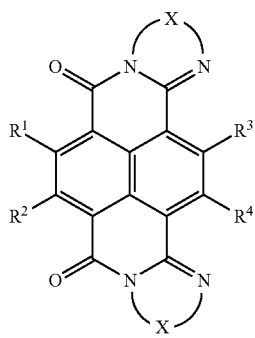

(I.c2)

in which the R$^1$, R$^2$, R$^3$ and R$^4$ radicals, which are each Br in the compound Ia) obtained in step a), are each F or CN, and some of the R$^1$, R$^2$, R$^3$ and R$^4$ radicals which are each Br in the compound Ia) obtained in step a), may also be hydrogen.

The imidation of the carboxylic anhydride groups in reaction steps c1) and a2) is known in principle. Preference is given to effecting the reaction of the dianhydride with the primary amine in the presence of a polar aprotic solvent. Suitable polar aprotic solvents are nitrogen heterocycles, such as pyridine, pyrimidine, quinoline, isoquinoline, quinaldine, N-methylpiperidine, N-methylpiperidone and N-methylpyrrolidone.

The reaction may be undertaken in the presence of an imidation catalyst. Suitable imidation catalysts are organic and inorganic acids, for example formic acid, acetic acid, propionic acid and phosphoric acid. Suitable imidation catalysts are also organic and inorganic salts of transition metals such as zinc, iron, copper and magnesium. These include, for example, zinc acetate, zinc propionate, zinc oxide, iron(II) acetate, iron(III) chloride, iron(II) sulfate, copper(II) acetate, copper(II) oxide and magnesium acetate. An imidation catalyst is used preferably in the reaction of aromatic amines and is generally also advantageous for the reaction of cycloaliphatic amines. In the reaction of aliphatic amines, especially short-chain aliphatic amines, it is generally possible to dispense with the use of an imidation catalyst. The use amount of the imidation catalyst is preferably from 5 to 80% by weight, more preferably from 10 to 75% by weight, based on the total weight of the compounds to be amidated.

The molar ratio of amine to dianhydride is preferably from about 2:1 to 4:1, more preferably from 2.2:1 to 3:1.

The reaction temperature in steps c1) and a2) is generally from ambient temperature to 200° C., preferably from 40 to 180° C. The reaction of aliphatic and cycloaliphatic amines is effected preferably within a temperature range of from about 60° C. to 100° C. The reaction of aromatic amines is effected preferably within a temperature range of from about 120 to 160° C.

Preference is given to effecting the reaction in reaction steps c1) and a2) under a protective gas atmosphere, for example nitrogen.

Reaction steps c1) and a2) may be effected at standard pressure or, if desired, under elevated pressure. A suitable pressure range is in the range from about 0.8 to 10 bar. When volatile amines are used (boiling point about ≦180° C.), preference is given to working under elevated pressure.

In general, the diimides obtained in reaction steps c1) and a2) may be used for the subsequent reactions without further purification. For use of the products as semiconductors, it may, however, be advantageous to subject the products to further purification. This includes, for example, column chromatography processes, where the products are preferably dissolved in a halogenated hydrocarbon such as methylene chloride, chloroform or tetrachloroethane and are subjected to a separation or filtration on silica gel. Finally, the solvent is removed.

The inventive compounds and those obtainable by the process according to the invention are suitable particularly advantageously as organic semiconductors. They function as n-semiconductors and are notable for their air stability. They also possess high charge transport mobility and have a high on/off ratio. They are suitable particularly advantageously for organic field-effect transistors. To prepare semiconductor materials, the inventive compounds may be processed further by one of the following processes: printing (offset, flexographic, gravure, screen, inkjet, electrophotography), evaporation, laser transfer, photolithography, drop casting. They are suitable in particular for use in displays and RFID tags.

The inventive compounds and those obtainable by the process according to the invention are also suitable particularly advantageously for data storage, in organic LEDs, in photovoltaics, as UV absorbers, as optical brighteners, for optical labels and as fluorescent labels for biomolecules such as proteins, DNA, sugars and combinations thereof.

The invention is illustrated in detail with reference to the nonrestrictive examples which follow.

EXAMPLES

Example 1

2,3,6,7-tetrabromonaphthalene-1,4:5,8-tetracarboxylic dianhydride

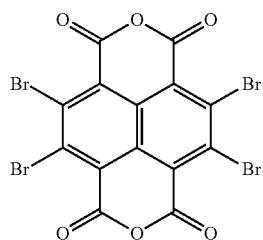

A solution of 2.68 g (10 mmol) of naphthalene-1,4:5,8-tetracarboxylic bisanhydride is added dropwise within 4 hours to a solution of 2.86 g (10 mmol) of dibromocyanuric acid in 30% oleum. After the addition has ended, the mixture is stirred at room temperature for another hour before it is poured onto 500 ml of ice-water. The precipitate is filtered off and washed to neutrality with water, washed with methanol and dried under reduced pressure. 3.5 g (60%) of the 2,3,6,7-tetrabromonaphthalene-1,4:5,8-tetracarboxylic dianhydride are obtained in the form of a yellowish solid.

Example 2

Mixture of Difluoro- and Tetrafluoronaphthalenetetracarboxylic Anhydrides

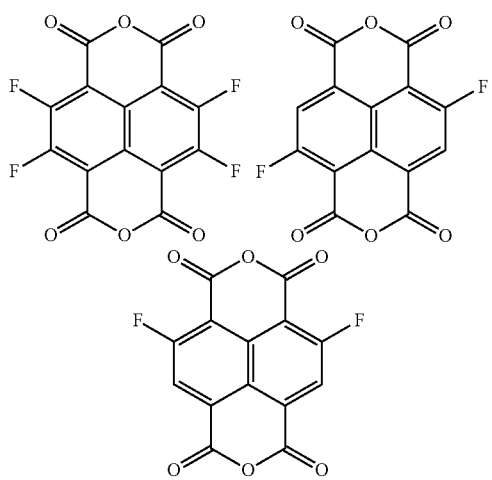

5 ml of thionyl chloride are added to 32 ml of anhydrous sulfolane, the mixture is heated to 130° C. and the volatile constituents are distilled off. The mixture is cooled to 100° C. Subsequently, 0.85 g (1 mmol) of the above-described tetrabromo bisanhydride compound is added thereto, and also 0.1 g of 18-crown-6 and 1.4 g (12 mmol) of dried potassium fluoride. The mixture is heated at 120° C. and kept at this temperature for 2 hours. Subsequently, the mixture is heated to 145° C. and kept at this temperature for 2 hours. The reaction mixture is cooled to room temperature, precipitated in water, filtered and washed with water. According to mass spectroscopy analysis, a mixture of difluoro- and tetrafluoronaphthalic bisanhydride, which comprises a trace of trifluoronaphthalic bisanhydride, is obtained.

Example 3

2,3,6,7-tetrabromonaphthalene-1,8;4,5-tetracarboxylic bisanhydride

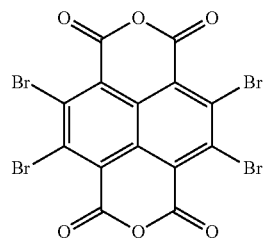

(further example for the preparation of the compound specified in example 1)

5.36 g (20 mmol) of 1,8;4,5-naphthalenetetracarboxylic bisanhydride are dissolved in 100 ml of 30% oleum within one hour. At room temperature, a solution of 12.6 g (44 mmol) of dibromoisocyanuric acid in 100 ml of 30% oleum is added to this solution within four hours. After the addition has ended, the reaction mixture is stirred for 16 hours and then poured cautiously onto 1000 ml of ice-water, in the course of which a solid precipitates out. The residue is washed with dilute hydrochloric acid and a little methanol and dried under reduced pressure. 10.8 g (92%) of a yellow solid are obtained.

Example 4

2,6-dibromonaphthalene-1,8;4,5-tetracarboxylic bisanhydride
2,7-dibromonaphthalene-1,8;4,5-tetracarboxylic bisanhydride

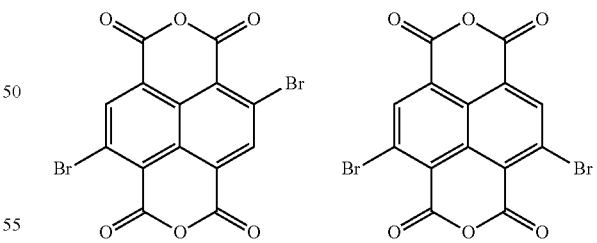

At room temperature, a solution of 3.44 g (12 mmol) of dibromoisocyanuric acid in 100 ml of 20% oleum is added to a solution of 2.68 g (10 mmol) of 1,8;4,5-naphthalenetetracarboxylic bisanhydride in 50 ml of 20% oleum within four hours. After the addition has ended, the mixture is stirred for another hour before the reaction mixture is added to 2000 ml of ice-water. The mixture is stirred at room temperature for 16 hours, filtered and washed with dilute hydrochloric acid and with methanol, and dried. 3.4 g (80% of a yellow solid with a bromine value of 36.6% (theoretically 37.5%) are obtained).

According to ¹H NMR in $D_2SO_4$, the product consists of a 1:1 isomer mixture of the two abovementioned compounds.

Example 5

Condensation of ortho-phenylenediamine with
2,6-dibromonaphthalene-1,8;4,5-tetracarboxylic bisanhydride
2,7-dibromonaphthalene-1,8;4,5-tetracarboxylic bisanhydride

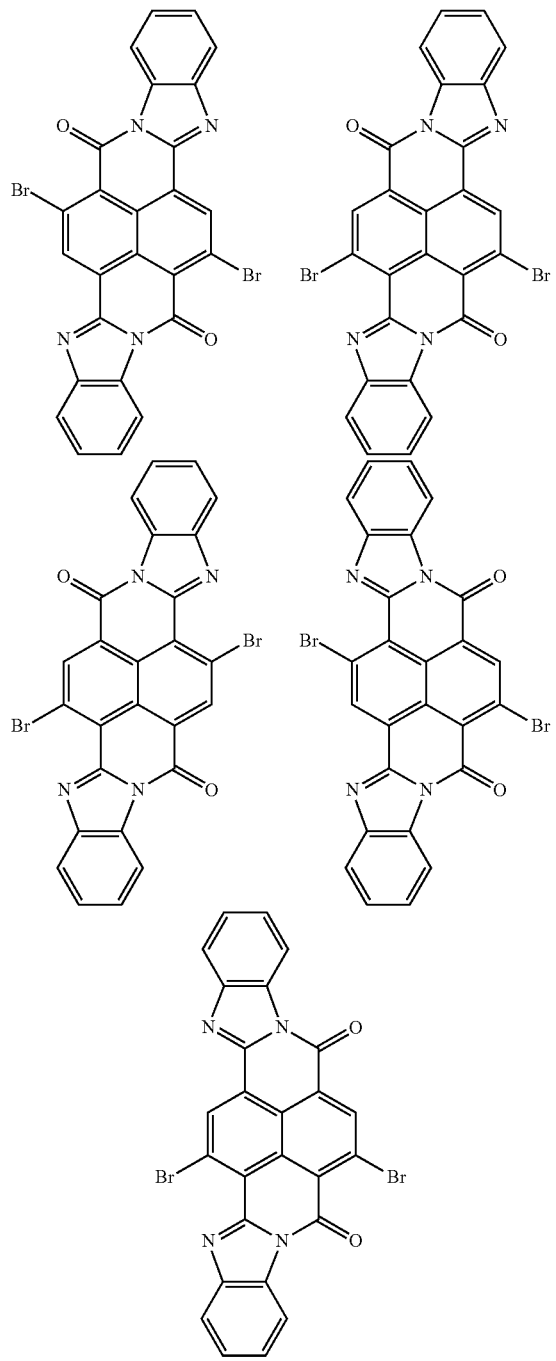

0.21 g (0.5 mmol) of dibromonaphthalenetetracarboxylic bisanhydride is heated to 80° C. in a mixture of 2.5 g of phenol, 0.12 g (1.1 mmol) of ortho-phenylenediamine and 0.09 g (11 mmol) of pyrazine. The reaction mixture is kept at this temperature for 4 hours, then 2.5 ml of methanol are added, and the mixture is cooled to room temperature and filtered. The residue is washed with methanol and dried. 0.19 g (67%) of a blue-black solid is obtained.

Example 6

Condensation of 1,8-diaminonaphthalene with
2,6-dibromonaphthalene-1,8;4,5-tetracarboxylic bisanhydride
2,7-dibromonaphthalene-1,8;4,5-tetracarboxylic bisanhydride

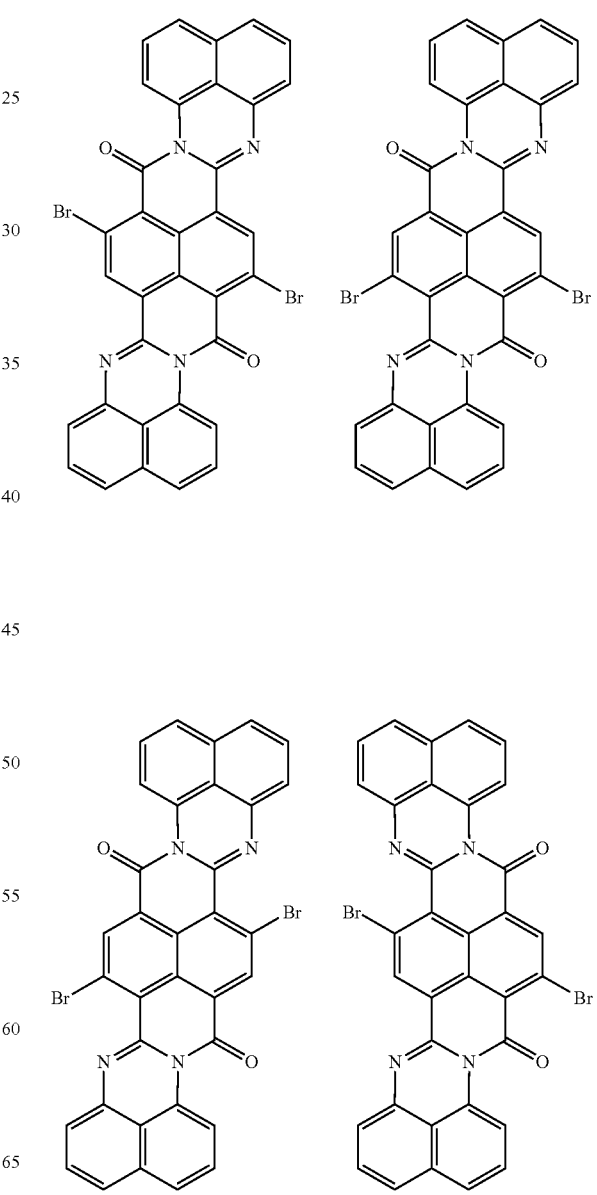

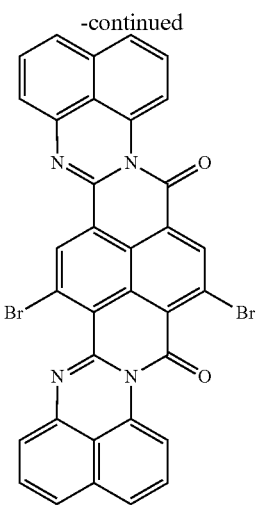

A mixture of 130 g of phenol, 11.0 g (26 mmol) of dibromonaphthalenetetracarboxylic bisanhydride, 9.36 g (57 mmol) of 1,8-diaminonaphthalene and 4.68 g (57 mmol) of pyrazine is heated to 80° C. for four hours. After cooling to room temperature, 130 ml of methanol are added, and the reaction mixture is stirred for a further 16 hours and filtered. The blue-black residue is washed with methanol and then with warm water and dried in a vacuum drying cabinet.

Example 7

2,3,6,7-Tetracyanonaphthalene-1,8;4,5-tetracarboxylic bisanhydride

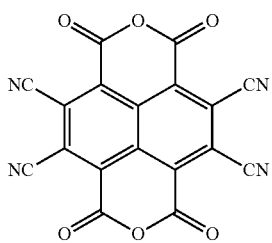

A mixture of 0.58 (1 mmol) of 2,3,6,7-tetrabromonaphthalene-1,8;4,5-tetracarboxylic dianhydride in 50 ml of dioxane is admixed with 1.76 g (15 mmol) of zinc cyanide, 70 mg (0.143 mmol) of 1,1'-bis(diphenylphosphinoferrocene) and 79 mg (143 mmol) of tris(dibenzylideneacetone)dipalladium. The mixture is stirred at 100° C. for 22 hours. 5 ml of sulfolane are added and the mixture is stirred at reflux for a further 97 hours. Subsequently, the reaction mixture is diluted with water and the residue which forms is filtered off, washed with water and dried. 0.46 g of a solid is obtained.

Example 8

N,N'-Bis(phenylethyl)-2,6-dibromonaphthalene-1,8;4,5-tetracarboximide N,N'-Bis(phenylethyl)-2,7-dibromonaphthalene-1,8;4,5-tetracarboximide by imidation of 2,3,6,7-tetrabromonaphthalene-1,4;5,8-tetracarboxylic bisanhydride

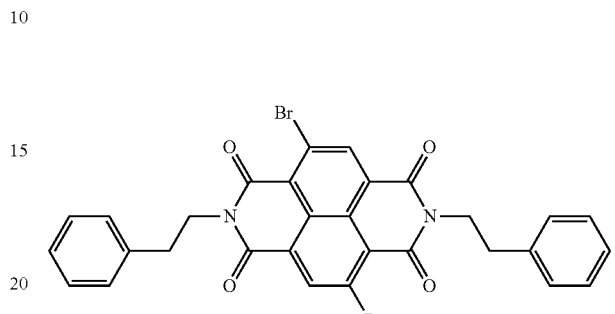

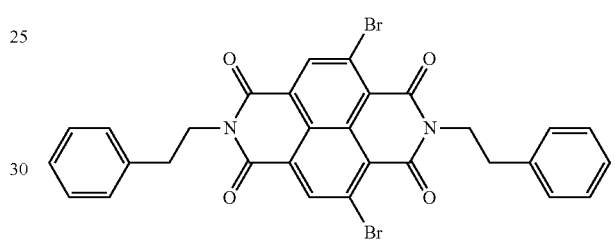

A mixture of 25 ml of xylene, 2.3 g (4 mmol) of 2,3,6,7-tetrabromonaphthalene-1,8;4,5-tetracarboxylic bisanhydride, 1.94 g (16 mmol) of phenethylamine is heated to 85° C. for 6 hours and then to 110° C. for one hour. The reaction mixture is cooled to room temperature and filtered, and the residue is washed with ethanol. 2.3 g of a solid product are obtained.

Example 9

N,N'-Di(2,6-diisopropylphenyl)-2,3,6,7-tetrabromonaphthalene-1,8;4,5-tetracarboximide Napthalene-1,8;4,5-tetracarboxylic acid (200 mg, 0.343 mmol) and 2,6-diisopropylaniline (425 mg, 2.40 mmol) are initially charged in concentrated acetic acid (5 ml) and stirred at 120° C. for 6 h. This is followed by addition of water (50 ml), neutralization with saturated sodium hydrogencarbonate solution and extraction with chloroform. The combined organic phases are dried over sodium sulfate and freed of the solvent. The residue is eluted with pentane/dichloromethane=2/1 on silica gel. The target compound is isolated as the second, pale yellow fraction. It can be obtained in pure form by preparative HPLC (RP18) with dichloromethane/methanol=16/84.

Yield: 51 mg (0.051 mmol, 15%)

ESI-MS: calc. for $C_{50}H_{53}Br_3N_3O_4$ [M+H]$^+$: 1000.1558. found: 1000.1478; calc. for $C_{50}H_{52}Br_3NaN_3O_4$ [M+Na]$^+$: 1022.1378. found: 1022.1303.

m.p.: 344.5-346° C.

39

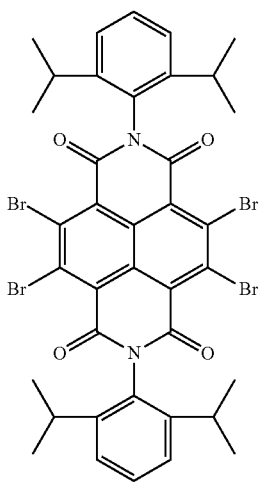

Example 10

2,3,6,7-Tetrabromonaphthalene-1,8;4,5-tetracarboximide

Naphthalene-1,4,5,8-tetracarboxylic acid (500 mg, 0.857 mmol) and ammonium acetate (1.32 g, 17.1 mmol) are heated to reflux with concentrated acetic acid to initially form a yellow solution. Later, an orange solid precipitates out, which is filtered off while hot after 2 h. The substance is washed with concentrated acetic acid (3 ml), water (5 ml), sat. sodium hydrogencarbonate solution (3 ml) and water again (5 ml), and then dried over phosphorus pentoxide.

Yield: 150 mg (0.258 mmol, 30%)
EI-MS: calc. for $C_{14}H_2Br_4N_2O_4$ [M]$^+$: 581.7. found: 581.7
m.p. >350° C.

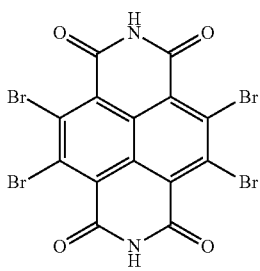

What is claimed is:
1. A compound of the general formula I

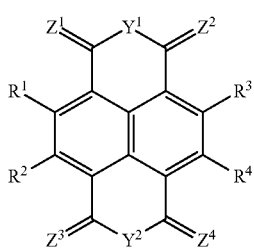

where
at least one of the $R^1$, $R^2$, $R^3$ and $R^4$ radicals is a substituent which is selected from Br, F and CN, and the remaining radicals are each hydrogen,

40

$Y^1$ is O or NR$^a$, where R$^a$ is hydrogen or an organyl radical,
$Y^2$ is O or NR$^b$, where R$^b$ is hydrogen or an organyl radical,
$Z^1$ and $Z^2$ are each independently O or NR$^c$, where R$^c$ is an organyl radical,
$Z^3$ and $Z^4$ are each independently O or NR$^d$, where R$^d$ is an organyl radical,
where, in the case that $Y^1$ is NR$^a$ and at least one of the $Z^1$ and $Z^2$ radicals is NR$^c$, R$^a$ with one R$^c$ radical may also together be a bridging group having 2 to 5 atoms between the flanking bonds, and
where, in the case that $Y^2$ is NR$^b$ and at least one of the $Z^3$ and $Z^4$ radicals is NR$^d$, R$^b$ with one R$^d$ radical may also together be a bridging group having 2 to 5 atoms between the flanking bonds,
and provided that one of the following conditions apply:
a) three of the $R^1$, $R^2$, $R^3$ and $R^4$ radicals are each bromine or are each fluorine or are each cyano, and the remaining radical is hydrogen;
b) $R^1$ and $R^2$ are each independently selected from fluorine and cyano, and $R^3$ and $R^4$ are each hydrogen;
c) $R^1$ and $R^3$ are each independently selected from fluorine and cyano, and $R^2$ and $R^4$ are each hydrogen; or
d) $R^1$ and $R^2$ are each bromine, and $R^3$ and $R^4$ are each hydrogen.

2. The compound according to claim 1, wherein three of the $R^1$, $R^2$, $R^3$ and $R^4$ radicals are each bromine or are each fluorine or are each cyano, and the remaining radical is hydrogen.

3. The compound according to claim 1, wherein $R^1$ and $R^2$ are each independently selected from fluorine and cyano, and $R^3$ and $R^4$ are each hydrogen.

4. The compound according to claim 1, wherein $R^1$ and $R^3$ are each independently selected from fluorine and cyano, and $R^2$ and $R^4$ are each hydrogen.

5. The compound according to claim 1, wherein $R^1$ and $R^2$ are each bromine, and $R^3$ and $R^4$ are each hydrogen.

6. A compound of the formula:

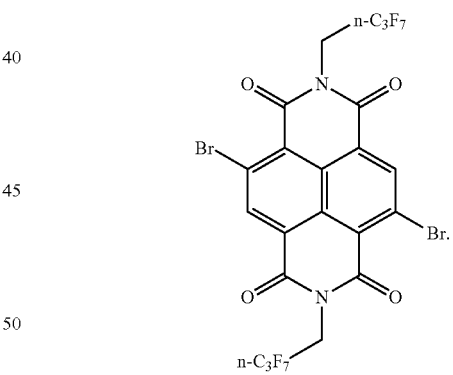

7. A semiconductor comprising the compound of the general formula I as defined in claim 1.

8. A semiconductor comprising the compound of claim 6.

9. The compound according to claim 2, wherein three of the $R^1$, $R^2$, $R^3$ and $R^4$ radicals are each bromine, and the remaining radical is hydrogen.

10. The compound according to claim 2, wherein three of the $R^1$, $R^2$, $R^3$ and $R^4$ radicals are each fluorine, and the remaining radical is hydrogen.

11. The compound according to claim 2, wherein three of the $R^1$, $R^2$, $R^3$ and $R^4$ radicals are each cyano, and the remaining radical is hydrogen.

* * * * *